(12) United States Patent
Lawless

(10) Patent No.: US 6,592,731 B1
(45) Date of Patent: Jul. 15, 2003

(54) AMPEROMETRIC OXYGEN SENSOR

(75) Inventor: William N. Lawless, Westerville, OH (US)

(73) Assignee: CeramPhysics, Inc., Westerville, OH (US)

( * ) Notice: Subject to any disclaimer, the term of this patent is extended or adjusted under 35 U.S.C. 154(b) by 0 days.

(21) Appl. No.: 09/662,773

(22) Filed: Sep. 15, 2000

Related U.S. Application Data

(60) Provisional application No. 60/155,817, filed on Sep. 23, 1999.

(51) Int. Cl.$^7$ .............................................. G01N 27/407
(52) U.S. Cl. ...................... 204/425; 204/426; 204/408; 205/785
(58) Field of Search ................................ 204/421–429, 204/408; 205/781, 783.5, 784, 784.5, 785

(56) References Cited

U.S. PATENT DOCUMENTS

| | | |
|---|---|---|
| 3,400,054 A | 9/1968 | Ruka et al. |
| 3,768,259 A | 10/1973 | Carnahan et al. |
| 3,819,500 A | 6/1974 | Van Esdonk et al. |
| 3,859,192 A | 1/1975 | Barnes et al. |
| 3,871,981 A * | 3/1975 | Flais et al. |
| 3,909,385 A | 9/1975 | Spielberg et al. |
| 3,948,813 A | 4/1976 | Holcombe, Jr. et al. |
| 3,974,054 A | 8/1976 | Poolman et al. |
| 4,021,326 A * | 5/1977 | Pollner et al. |
| 4,195,119 A | 3/1980 | Kummer |
| 4,207,159 A | 6/1980 | Kimura et al. |
| 4,208,265 A | 6/1980 | Hori et al. |
| 4,218,297 A | 8/1980 | Henault et al. |
| 4,231,231 A | 11/1980 | Lawless |
| 4,296,147 A | 10/1981 | Lawless |
| 4,296,607 A | 10/1981 | Lawless |
| 4,296,608 A | 10/1981 | Lawless |
| 4,354,355 A | 10/1982 | Lawless |

(List continued on next page.)

FOREIGN PATENT DOCUMENTS

| | | |
|---|---|---|
| EP | 0 726 226 A1 | 8/1996 |
| EP | 0778 069 A1 | 6/1997 |
| WO | WO 95/08360 | 3/1995 |

OTHER PUBLICATIONS

Takehiko Takahashi and Hiroyasu Iwahara; "High Oxide Ion Conduction in Sintered Oxides of the System Bi2O3–WO3"; Journal of Applied Electrochemistry 3; jul. 1972; pp. 65–72.

*Primary Examiner*—T. Tung
(74) *Attorney, Agent, or Firm*—Killworth, Gottman, Hagan & Schaeff LLP

(57) ABSTRACT

A low cost amperometric oxygen sensor which utilizes a plurality of oxygen ion conductor layers interposed between a plurality of oxygen-porous electrode layers is provided. Oxygen from a sample gas enters the sensor at porous cathode electrodes, is pumped through the ion conductor layers, and exits through the anode electrodes. The amperometric current generated is representative of the partial pressure of oxygen in the sample gas. In accordance with one embodiment of the present invention, an amperometric oxygen sensor is provided for determining the oxygen partial pressure of a gas. The sensor comprises a sensor body defined by a plurality of oxygen-porous electrode layers and at least one oxygen ion conductor layer. The plurality of oxygen-porous electrode layers include at least one cathode layer and at least one anode layer. Each of the cathode layers define first and second major cathode surfaces and each of the anode layers defining first and second major anode surfaces. The oxygen ion conductor layer is interposed between the first major cathode surface and the first major anode surface. The cathode layer defines an unexposed second major cathode surface and a cathode end portion exposed along a first edge of the sensor body. The anode layer defines an unexposed second major anode surface and an anode end portion exposed along a second edge of the sensor body. The amperometric oxygen sensor further comprises a voltage source having a first pole connected to the cathode layer and a second pole connected to the anode layer, and a current meter connected to measure an amperometric current flowing through the at least one ion conductor layer.

12 Claims, 4 Drawing Sheets

U.S. PATENT DOCUMENTS

| | | |
|---|---|---|
| 4,356,235 A | 10/1982 | Lawless |
| 4,396,721 A | 8/1983 | Lawless |
| 4,449,990 A | 5/1984 | Tedford, Jr. |
| 4,462,891 A | 7/1984 | Lawless |
| 4,464,244 A * | 8/1984 | Uchida et al. |
| 4,502,939 A * | 3/1985 | Holfelder et al. |
| 4,515,534 A | 5/1985 | Lawless et al. |
| 4,541,899 A | 9/1985 | Mase et al. |
| 4,545,254 A | 10/1985 | Lawless et al. |
| 4,547,277 A | 10/1985 | Lawless |
| 4,547,281 A | 10/1985 | Wang et al. |
| 4,599,677 A | 7/1986 | Lawless et al. |
| 4,642,174 A | 2/1987 | Shibata |
| 4,684,207 A | 8/1987 | Lawless |
| 4,789,388 A | 12/1988 | Nishibata et al. |
| 4,885,142 A | 12/1989 | Suitor et al. |
| 4,918,421 A | 4/1990 | Lawless et al. |
| 5,009,763 A | 4/1991 | Hise |
| 5,034,023 A | 7/1991 | Thompson |
| 5,062,911 A | 11/1991 | Hampton et al. |
| 5,108,465 A | 4/1992 | Bauer et al. |
| 5,169,506 A | 12/1992 | Michaels |
| 5,183,965 A | 2/1993 | Lawless |
| 5,186,793 A | 2/1993 | Michaels |
| 5,205,990 A | 4/1993 | Lawless |
| 5,212,013 A | 5/1993 | Gupta et al. |
| 5,222,713 A | 6/1993 | Lawless et al. |
| 5,246,729 A | 9/1993 | Gupta et al. |
| 5,296,110 A | 3/1994 | Tabatabaie-Raissi |
| 5,302,258 A | 4/1994 | Renlund et al. |
| 5,385,874 A | 1/1995 | Renlund et al. |
| 5,393,399 A | 2/1995 | Van den Berg et al. |
| 5,397,443 A | 3/1995 | Michaels |
| 5,441,610 A | 8/1995 | Renlund et al. |
| 5,536,378 A | 7/1996 | Gibson et al. |
| 5,549,983 A | 8/1996 | Yamanis |
| 5,589,017 A | 12/1996 | Minh |
| 5,611,845 A | 3/1997 | Delp, II |
| 5,643,355 A | 7/1997 | Phillips et al. |
| 5,672,811 A * | 9/1997 | Kato et al. |
| 5,712,055 A | 1/1998 | Khandkar et al. |
| 5,731,097 A | 3/1998 | Miyashita et al. |
| 5,736,028 A * | 4/1998 | Hjortsberg et al. |
| 5,807,642 A | 9/1998 | Xue et al. |
| 5,855,762 A | 1/1999 | Phillips et al. |
| 5,865,877 A | 2/1999 | Delp, II |
| 5,905,000 A | 5/1999 | Yadav et al. |
| 5,922,178 A | 7/1999 | Isenberg |
| 5,961,929 A | 10/1999 | Lawless |
| 5,972,182 A | 10/1999 | Lawless |
| 6,033,457 A | 3/2000 | Lawless |

OTHER PUBLICATIONS

Advertisement for "Micro Oxivision Ratio Meter MO–1000"; NGK Spark Plug Co Ltd.

* cited by examiner

AMPEROMETRIC OXYGEN SENSOR

CROSS-REFERENCE TO RELATED APPLICATIONS

This application claims the benefit of U.S. Provisional Application Serial No. 60/155,817, filed Sep. 23, 1999.

BACKGROUND OF THE INVENTION

The present invention relates to a device for sensing the partial pressure of oxygen in a gas, and more particularly to an active multilayer sensor utilizing an oxygen ion conducting material.

It is widely recognized that one of the most important diagnostics for monitoring the efficiency of any combustion process is the measurement of the oxygen partial pressure in an exhaust gas. Thus, oxygen sensors have long been used to measure the oxygen content of exhaust gases from such diverse combustion processes as internal combustion engines in motor vehicles and coal, natural gas, or oil burning power generation facilities.

The most widely known and used oxygen sensors are based on partially stabilized zirconia (PSZ) as the ion conductor. Such sensors function by monitoring the electromotive force (EMF) developed across an ion conductor which is exposed to different partial pressures of oxygen. Oxygen tends to move from a gas containing a high concentration of oxygen to one of lower concentration. If two gases are separated from each other by an oxygen ion conductor, the oxygen molecules will dissociate on one surface of the conductor and absorb electrons to form oxygen ions. These ions then diffuse through the ionic conductor, leaving the entry surface with a deficiency of electrons ($O_2 + 4e \rightarrow 2O^{-2}$). On the exit or low oxygen concentration side of the conductor, oxygen ions leaving the conductor must give up electrons to form molecular oxygen, thus leaving the exit surface with an excess of electrons.

This creates the EMF between the two surfaces of the ion conductor. This EMF is described by the Nernst relation:

$$EMF = t_i \left(\frac{RT}{nF}\right) \ln\left(\frac{P_{O_2}}{P'_{O_2}}\right)$$

where $t_i$ is the ionic transference number, R is the gas constant, T is the absolute temperature, n is the number of electrons involved in the electrode reaction (in this case, n=4), F is the Faraday constant, and $P_{O_2}$ and $P'_{O_2}$ are the oxygen partial pressures of the first and second gases, respectively.

One problem with the use of partially stabilized zirconia sensors is that they must be operated at temperatures in the range of about 800° C. to reduce internal resistance to a point where a current can be measured. Further, the raw material costs of stabilized zirconia is relatively high, and the melting point of zirconia is quite high (2700° C.) so that formation of sensors is expensive.

Lawless, in U.S. Pat. No. 4,462,891, describes a passive oxygen sensor using ceramic ion conducting materials based on nickel niobates and Bismuth oxides. The oxygen sensor includes a plurality of layers of the ceramic material and a porous metallic conductor arranged to form a body having alternating ceramic and metallic layers, with first alternate ones of the metallic layers being exposed along one side of the body and second alternate ones of the metallic layers being exposed along an opposite side of the body. The first and second alternate ones of the metallic layers are exposed to separate gases, one of the gases being a reference gas, in order to create a voltage output signal across electrodes connected to alternate metallic layers. The voltage output signal is indicative of the relative oxygen partial pressures of the separate gases. Thus, the passive oxygen sensor cannot provide an oxygen partial pressure indication unless the first and second metallic layers present in the body are exposed, respectively, to a sample gas and a separate reference gas having a known oxygen partial pressure, i.e., each side of the sensor body must be exposed to a separate gas.

More recently, amperometric sensors have been introduced which also use partially stabilized zirconia but which do not require a reference gas to operate. Such a sensor 80 is illustrated in FIG. 1 and comprises a cavity 100 in communication with the unknown gas through a diffusion hole 120. The base of the cavity 100 is a PSZ electrolyte 140 which is connected through electrodes 160, 160' to a voltage source 170. The application of a voltage causes oxygen to be pumped from the cavity through diffusion into the surrounding gas as shown by the arrows. If the cavity is sealed atop the base, and if the top of the cavity has the small diffusion hole 120, then a point is reached on increasing the voltage where no more oxygen can be pumped out of the cavity than is entering through the diffusion hole. The current drawn at this point is called the amperometric current. The larger the oxygen partial pressure in the surrounding gas, the larger will be the amperometric current. Thus, a measurement of the amperometric current yields the oxygen partial pressure. Again, however, this sensor suffers from some of the same drawbacks in that materials and fabrication costs are relatively high. An extremely small diffusion hole is required, about 5 μm, and requires precise machining because the size is critical to the operation of the sensor. Additionally, the manufacture of the sensor of FIG. 1 requires five silk screen operations and four burnout steps. Finally, these sensors lose their sensitivity above about 80% oxygen and the diffusion hole is prone to plugging.

Accordingly, there remains a need in the art for an amperometric oxygen sensor which is relatively inexpensive to manufacture and provides enhanced oxygen sensitivity.

BRIEF SUMMARY OF THE INVENTION

The present invention meets that need by providing a low cost amperometric oxygen sensor which utilizes a plurality of oxygen ion conductor layers interposed between a plurality of oxygen-porous electrode layers. Oxygen from a sample gas enters the sensor at porous cathode electrodes, is pumped through the ion conductor layers, and exits through the anode electrodes. The amperometric current generated is representative of the partial pressure of oxygen in the sample gas.

In accordance with one embodiment of the present invention, an amperometric oxygen sensor is provided for determining the oxygen partial pressure of a gas. The sensor comprises a sensor body defined by a plurality of oxygen-porous electrode layers and at least one oxygen ion conductor layer. The plurality of oxygen-porous electrode layers include at least one cathode layer and at least one anode layer. Each of the cathode layers define first and second major cathode surfaces and each of the anode layers defining first and second major anode surfaces. The oxygen ion conductor layer is interposed between the first major cathode surface and the first major anode surface. The cathode layer defines an unexposed second major cathode surface and a cathode end portion exposed along a first edge of the sensor body. The anode layer defines an unexposed second major anode surface and an anode end portion exposed along a second edge of the sensor body. The amperometric oxygen sensor further comprises a voltage source having a first pole connected to the cathode layer and a second pole connected to the anode layer, and a current meter connected to measure an amperometric current flowing through the at least one ion conductor layer.

The oxygen porous electrode layers define an oxygen diffusion limit that is a function of electrode porosity and oxygen partial pressure of the gas. The oxygen ion conductor layer and the oxygen pump potential define an oxygen pump rate. The oxygen pump rate may be greater than the oxygen diffusion limit.

Preferably, a plurality of cathode layers are provided and electrically connected along the first edge of the sensor body with a first oxygen-porous termination. Similarly, a plurality of anode layers are preferably provided and electrically connected along the second edge of the sensor body with a second oxygen-porous termination.

The sensor body preferably includes a heating circuit. The heating circuit may include a controller programmed to control the resistance of heating electrodes associated with the sensor body by applying a constant current to the heating electrodes and controlling the voltage applied to the heating electrodes. The controller may be further programmed to modulate the pulse width of the constant current to control the heating power applied to the heating electrodes and maintain a constant sensor temperature. The heating circuit comprises at least one heater electrode arranged in a co-planar relationship with at least one of the porous electrode layers. The heater electrode preferably comprises a pair of co-planar heater electrodes separated by a porous electrode material and electrically connected by an interconnect electrode. The interconnect electrode may be arranged on a dielectric cover plate. The interconnect electrode preferably comprises a non-porous electrode and the heater electrode preferably comprises an oxygen-porous electrode.

The oxygen ion conductor layer may comprise a ceramic electrolyte and the oxygen ion conductor layer may comprise partially stabilized zirconia. The oxygen-porous electrode layers may comprise oxygen-porous platinum and may be stabilized against sintering.

The gas may comprise nitrous oxide and the oxygen-porous electrode layers may comprise porous rhodium configured to catalyze dissociation of nitrous oxide into $N_2$ and $O_2$. In this manner, the amperometric current relates to the nitrous oxide content of the gas. For the purposes of defining and describing the present invention it is noted that the term "comprise" is utilized herein in the non-exclusive sense and that a gas, for example, comprising a particular substance may also comprise additional substances.

In accordance with another embodiment of the present invention, a method of determining the partial pressure of oxygen in a gas is provided comprising the steps of: exposing an amperometric oxygen sensor to a gas whose partial pressure is to be determined; connecting a first pole of a voltage source to the at least one cathode layer and a second pole of the voltage source to the at least one anode layer; and measuring an amperometric current flowing through the plurality of ion conductor layers.

Preferably, the sensor body is heated to approximately 550–800° C. and the sensor body includes a heating circuit associated with the sensor body. The method may further comprise the step of controlling a resistance of heating electrodes associated with the sensor body by applying a constant current to the heating electrodes and controlling the voltage applied to the heating electrodes. The pulse width of the current may be modulated to control the heating power applied to the heating electrodes and maintain a constant sensor temperature.

According to yet another embodiment of the present invention, a method of producing an amperometric oxygen sensor is provided. The method comprises the steps of: providing an unsintered sensor body, the unsintered sensor body being defined by a plurality of oxygen-porous electrode layers interposed between respective oxygen ion conductor layers; selecting a target porosity for the oxygen-porous electrode layers; selecting a sintering temperature for the sensor body, wherein the sintering temperature is selected to correspond to the target porosity for the oxygen-porous electrode layers; and sintering the sensor body at the selected sintering temperature to yield a sintered sensor body including oxygen porous electrode layers having the target porosity.

Accordingly, the present invention provides a low cost amperometric oxygen sensor which is easy to construct and provides enhanced oxygen sensitivity through amperometric measurement of oxygen partial pressures in a multilayer ceramic capacitor structure.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION OF THE PREFERRED EMBODIMENTS

Figure 1:
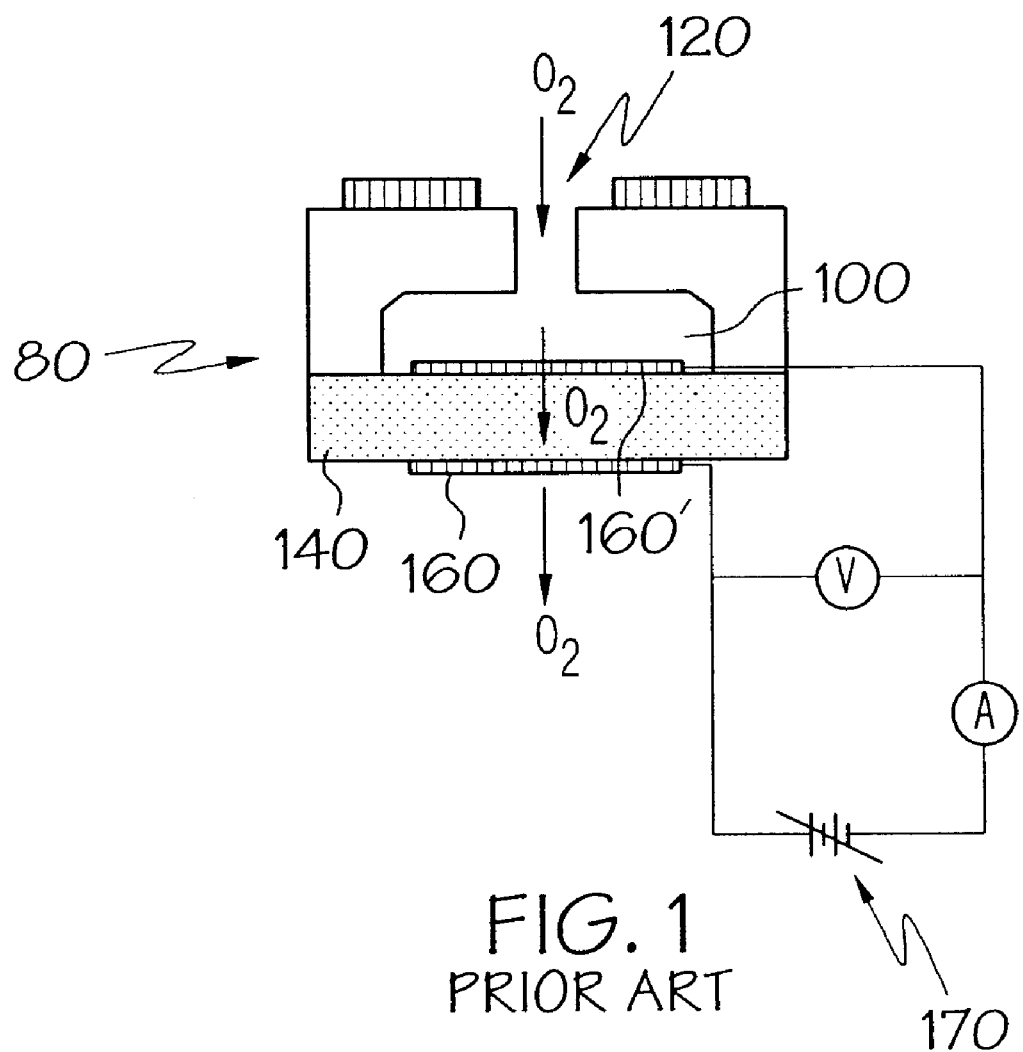
FIG. 1 is a schematic representation of a prior art oxygen sensor.
Figure 2:
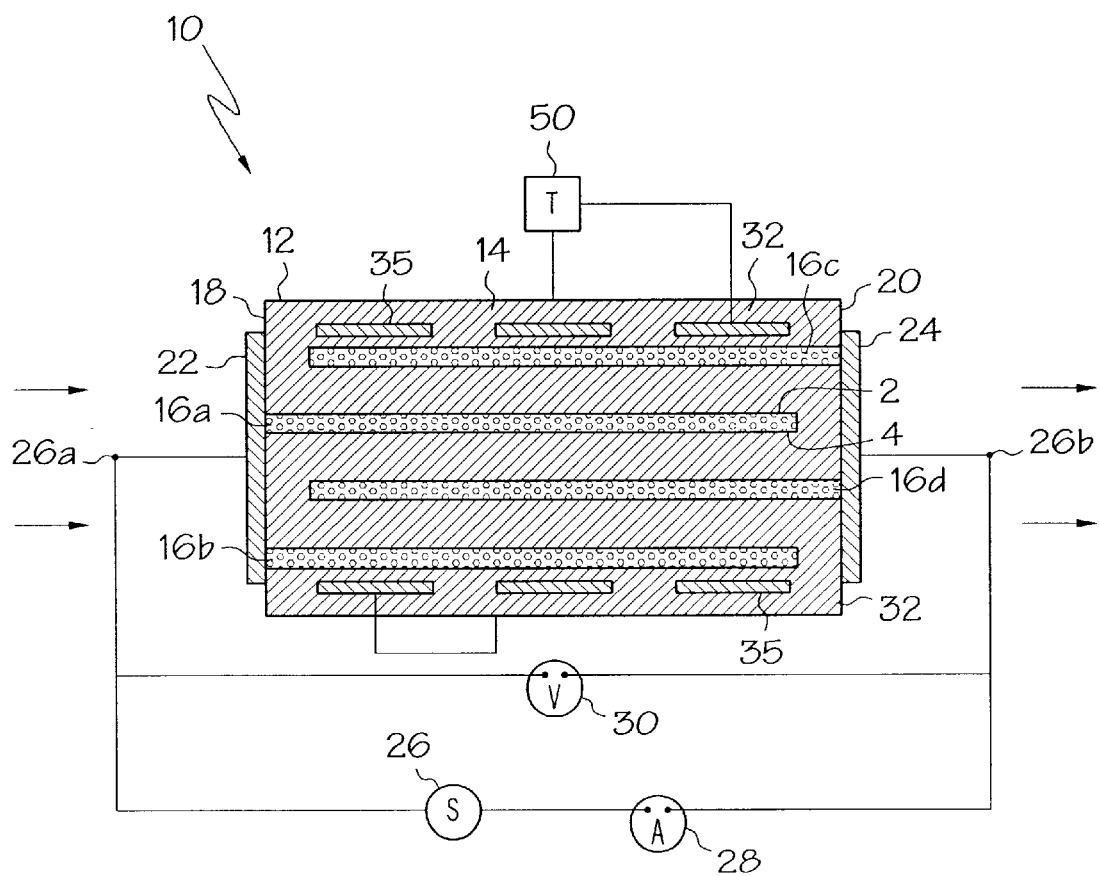
FIG. 2 is a schematic representation of an oxygen sensor in accordance with the present invention.

A schematic representation of an amperometric oxygen sensor constructed according to the present invention is shown in FIG. 2. As seen in FIG. 2, oxygen sensor 10 includes a sensor body 12 having alternating layers of an oxygen ion conducting material 14 and an oxygen-porous electrically conductive material 16a, 16b, 16c, 16d. A first set of oxygen-porous conductive layers 16a and 16b have end portions which are exposed along a first edge 18 of the sensor body 12. For the purpose of describing and defining the present invention, an oxygen ion conductor is any material capable of achieving electrical conductivity due to displacement of oxygen ions within its crystal lattice.

Electrical connections are made to the conductive layers 16a and 16b by firing F; electrically conductive oxygen-porous terminations 22 onto the ends of the conductive layers 16a, 16b to form a plurality of cathode layers. A second set of oxygen-porous conductive layers 16c and 16d have end portions which are exposed along a second edge 20 of the sensor body 12. The conductive layers 16c and 16d are electrically connected to one another by an electrically conductive oxygen-porous termination 24, to form a plurality of anode layers. Silver or oxygen-porous platinum are suitable materials for use as the electrically conductive oxygen-porous terminations 22, 24. The terminations 22, 24 are used to electrically connect the ceramic layers in parallel to reduce the electrical resistance of the sensor and allow increased amperometric current.

Each of the conductive layers 16a–16d include two major surfaces. For example, conductive layer 16a includes major surfaces 2 and 4. Each oxygen ion conductor layer 14 is disposed between major surfaces of opposing conductive layers. Further, both major surfaces of each conductive layer are unexposed, i.e., enclosed by the sensor body 12. It is contemplated by the present invention that any number of oxygen-porous conductive layers and ion conductor layers may be used to construct the sensor body 12. The number of layers shown in FIG. 2 is merely presented for illustrative purposes.

A voltage source 26 is electrically connected to the terminations 22 and 24 such that a first pole 26a of the voltage source 26 is electrically connected to the cathode layers formed by conductive layers 16a and 16b and a second pole 26b of the voltage source 26 is electrically connected to the anode layers formed by conductive layers 16c and 16d. An amperometric current meter 28 is connected between the voltage source 26 and the termination 24. A voltage meter 30 is connected across the voltage source 26.

The oxygen-porous electrically conductive material forming conductive layers 16a–d preferably comprises oxygen-porous platinum, although any suitable electrically conductive material which is porous to oxygen and catalyzes oxygen molecules to ions at the cathode layers and catalyzes ions to oxygen molecules at the anode layers may be used.

Platinum electrodes can be made porous to oxygen by well known methods. For example, the use of coarse Pt particles in an electroding ink results in porous electrodes. Other additions to the electroding ink, such as zirconia particles, further increase the porosity. A platinum electrode having 5–30% of its volume occupied by pores is one preferred example. As another example, 85 parts, by weight, of a coarse Pt powder available as platinum powder number 6432\0101 from Demetron, GMBH, Hanau, Germany, may be combined with 15 parts, by weight, of a 400 mesh zirconia powder in a suitable silk screening slurry.

In one embodiment of the present invention, the width of the sensor body 12, i.e., the dimension of the sensor body from the first edge 18 to the second edge 20, is about 0.20" (0.5 cm), the short ends of the conductive layers 16a, 16b, 16c, 16d terminate about 0.030" (0.075 cm) from respective side edges, leaving a 0.14" (0.36 cm) conductive layer overlap. The length of the sensor body 12 is about 0.18" (0.46 cm). The thickness of the sensor body 12 is defined by the number and thickness of the oxygen ion conductor layers 14, the conductive layers 16a, 16b, 16c, 16d, and any layers dedicated to a heating circuit (described below). In one embodiment of the present invention, eleven oxygen ion conductor layers 14 are positioned between alternate ones of twelve conductive layers 16a, 16b, 16c, 16d. The oxygen ion conductor layers 14 may comprise 0.0030" (0.076 mm) thick yttria-stabilized zirconia layers. The conductive layers comprise 0.0001" (0.0025 mm) thick porous platinum. The result is an oxygen sensor that is relatively compact in size and relatively inexpensive to produce.

A number of ceramic oxygen ion conductor materials may be used in accordance with the present Invention. Indeed, the present invention's advantages of simplicity of construction and reduced electrical resistance due to sensor geometry are applicable to any of a wide variety of ceramic materials used. Preferably, the oxygen ion conductor of the present invention is a ceramic electrolyte and more specifically, comprises yttria-stabilized zirconia ($ZrO_2$ stabilized with $Y_2O_3$) but may also comprise stabilized bismuth oxide, stabilized ceria, etc. The zirconia ceramic may be stabilized with materials other than $Y_2O_3$.

Fine grain sized powders of $ZrO_2$:$Y_2O_3$ can be sintered to high density at 1150–1300° C., making it possible to manufacture multi-layer sensor bodies from this oxygen ion conductor. Because of the convenient sintering temperatures of the ceramic materials of the present invention, the ceramics can be "tape cast" into a monolithic body. As is well known in the ceramic art, tape casting is a process for making a multilayered body (for example, a ceramic capacitor) wherein appropriate metal electrodes are interdispersed between the ceramic layers. A tape casting technique may be employed such as that described in U.S. Pat. No. 4,462,891, incorporated herein by reference. The ceramic layers are quite thin, having a thickness of from about 25–100 $\mu$m. Further, this tape casting method requires only a single silk screening operation and a single burnout step.

Higher porosity levels in the conductive layers are more suitable for sensing very low levels of oxygen in a gas, e.g., as low as 1 ppm oxygen partial pressure. Conversely, lower porosity levels in the conductive layers are more suitable for sensing applications over a broad range of oxygen partial pressure up to a maximum of $10^6$ ppm. According to one embodiment of the present invention, the amperometric oxygen sensor 10 is produced by sintering the entire sensor body 12, i.e., the oxygen ion conductor layers 14, the conductive layers 16a, 16b, 16c, 16d, and any layers dedicated to the heating circuit 12, at a sintering temperature selected to yield a predetermined oxygen porosity in the conductive layers 16a, 16b, 16c, 16d. Sintering at relatively high temperatures for relatively large amounts of time decreases the porosity in the electrode layers because the density of the sensor body increases. Conversely, sintering at relatively low temperatures for relatively short amounts of time does not lead to equally significant decreases in porosity in the electrode layers because the density of the sensor body does not increase as much as is the case for higher temperature and longer duration sintering.

Accordingly, an amperometric oxygen sensor according to the present invention may be produced by providing an unsintered sensor body, selecting a target porosity for the oxygen-porous electrode layers, and selecting a corresponding sintering temperature for the sensor body. The sintering temperature is selected to correspond to the target porosity and may be determined through experimentation. The sensor body is sintered at the selected sintering temperature to yield a sintered sensor body including oxygen porous electrode layers having a target porosity. For example, where the conductive layers comprise 0.0001" (0.0025 mm) thick oxygen porous platinum, and the sensor body is sintered at about 1200° C., for a duration of about 2 hours, the sintered sensor body is suitable for oxygen sensing up to the $10^6$ ppm maximum. In contrast, if the sensor body is sintered at a higher temperature, e.g., 1275° C., for the same duration, the sintered sensor body is more suitable for oxygen sensing down to the 1 ppm minimum.

There may be some increase in resistance in the oxygen porous electrode layers over time as a result of sintering of platinum particles in the electrodes at the operating temperature of the sensor. The long term stability of sensors according to the present invention may be improved in some instances by stabilizing the oxygen porous electrode layers against sintering. Rosemount Analytical, Inc. (www.frco.com) has developed a proprietary method for stabilizing platinum electrodes against sintering.

In operation, the oxygen sensor 10 is immersed in a gas whose oxygen partial pressure is to be determined. If there is not already oxygen present in the porous conductive layers 16a–d, oxygen from the gas passes through the porous terminations 22 and 24 and enters the porous electrodes 16a–d through diffusion. A voltage from voltage source 26 is applied across the terminations 22 and 24. The resulting voltage difference between the conductive layers 16a and 16b, also referred to herein as the cathode layers, and the conductive layers 16c and 16d, also referred to herein as the anode layers, will cause oxygen to be pumped through the layers of oxygen ion conducting material 14. Since the porous electrode layers 16a–d catalyze oxygen molecules to ions at the cathode layers 16a, 16b and catalyze ions to oxygen molecules at the anode layers 16c, 16d, oxygen enters at the cathode layers 16a, 16b, is pumped through the layers of ion conductor material 14, and exits through the anode layers 16c, 16d. The resulting electrical current is measured by the amperometric meter 28 and is indicative of the oxygen partial pressure of the gas.

Sensors based on stabilized zirconia tend to have operating temperatures above 700° C. The applied voltage is monitored by the voltage meter 30. It has been found that applied dc voltages at and above 0.2 volts often lead to instabilities in the sensor and that an applied voltage of 0.05 volts has been found to yield unstable current signals at large oxygen partial pressures. An applied voltage of 0.1 volts is the preferred bias voltage. The voltage source may be a dc voltage source or an ac voltage source operating at about 3 Hz. The preferred ac frequency is less than 50 Hz since, as the ac frequency increases, the sensor response to oxygen decreases. Because the oxygen sensor of the present invention operates at an elevated temperature, it is preferable to provide a heater and thermometer for the sensor body.

Figure 3:
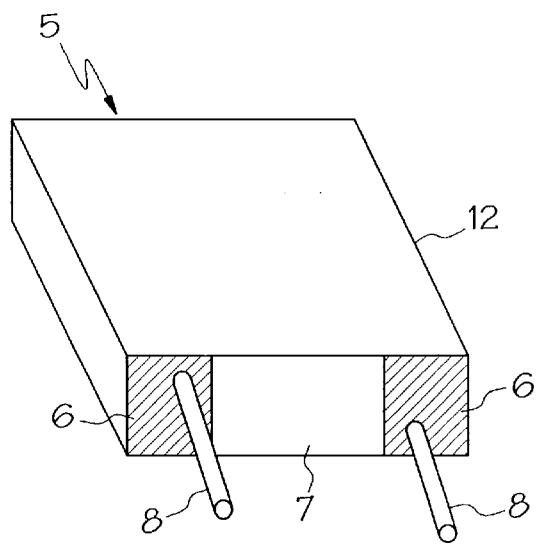
FIGS. 3–5 are illustrations of an alternative heating circuit arrangement according to the present invention.
Figure 4:
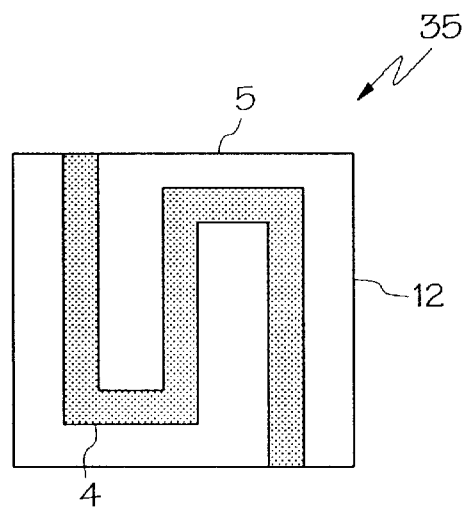
Figure 5:
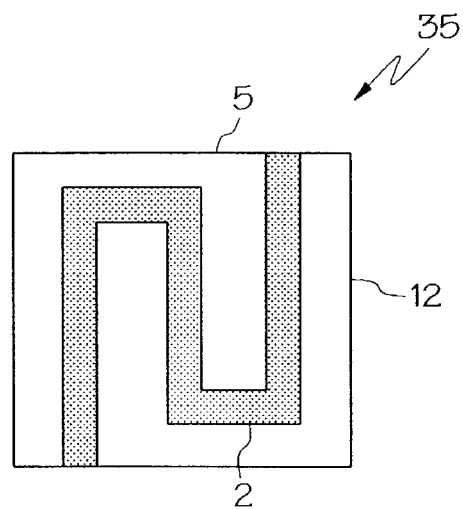

Resistive heating electrodes 35 are provided in the manner illustrated in FIGS. 2–5. As is illustrated in FIGS. 2–5, cover plate heating electrodes 35 in the form of platinum tracks are embedded in the ion conductor material 14 of the sensor body 12, more 25 specifically in the top and bottom cover plates 32. Referring specifically to FIGS. 3–5, the sensor body 12 is provided with a top heater track 2 and a bottom heater track 4. The rear face 5 of the sensor body 12 is provided with a conductive termination arranged to couple conductively the top heater track 2 to the bottom heater track 4. In addition, the front face 7 of the sensor body 12 is provided with a pair of conductive terminations 6 coupled conductively to respective ones of the top heater track 2 and the bottom heater track 4. In this manner, a complete circuit is formed by coupling a heating voltage source (incorporated in heating circuit controller 50) and terminals 8 to respective ones of the conductive terminations 6.

The measured resistance in the embedded platinum heater track 35 typically varies from about 2.3 to about 6.5 ohms between 25° C. and 800° C., respectively. The measured heater power required to maintain the sensor body 12 ranges up to about 2 watts at 800° C., a preferred sensor operating temperature. A heating voltage is applied across the heating circuit by connecting a heating voltage source across the heating electrodes 35. The resistivity of the heating circuit generates heat when a voltage is applied. The resistance of the heating electrodes 35 varies as a function of temperature. This temperature/resistance relation provides a means for measuring the temperature of the sensor body 12. Preferably, the heating electrodes 35 are coupled to a heating circuit controller 50 programmed to control the resistance of the heating electrodes 35 by applying a constant current to the heating electrodes 35 and controlling the voltage applied thereto.

The top and bottom cover plates 32 preferably comprise a 0.02" (0.05 cm) thick dielectric material (not shown) added above and below the uppermost and lowermost electroded layers of the sensor body 12 for electrical insulation and structural integrity. The sensor body 12 may be incorporated into a four pin package, two connections for the heating circuit, a cathode connection, and an anode connection, surrounded by thermal insulation, and enclosed by a Teflon particulate filter.

Conductive Au or Pt leads may be coupled to the various sensor electrodes by attaching the leads to the exposed electrode portions on the sensor body 12 with an Au or Pt paste. Alternatively, sensor packaging can be simplified by embedding the conductive leads in the sensor body 12. Specifically, small holes (~0.6 mm) may be drilled in the sensor body 12 prior to sintering and Pt or Au wires may be inserted, with a suitable conductive paste, into the holes.

A preferred heating control scheme involves applying the constant current to the heater electrodes 35 in square-wave pulses and using the voltage signal to control the pulse width of the current pulses (pulse-width modulation). Under feedback control the pulse width is modulated to maintain the voltage constant, thereby maintaining the resistance of the heating electrodes 35 constant, as desired. Stated differently, modulating the pulse width of the current controls the heating power applied to the heating electrodes 35 to maintain the sensor temperature constant. The voltage can easily be read using a 16 bit A/D converter to an accuracy of ±0.0015%. Conventional current control schemes allow maintenance of a constant current within about 0.01%. Therefore, the temperature of the integrated sensor body can be controlled within acceptable ranges.

A preferred microprocessor-based heating circuit controller 50 consists of a temperature-control section and a sensor-output section. The latter section would supply a constant voltage to the heating electrodes 35 and read the amperometric current in the heating electrodes 35. The current signal may be converted to a readout of the oxygen partial pressure and may be converted to an output suitable for controlling a combustion process.

The sensor 10 may be calibrated and used by first identifying the resistance of the heating electrodes 35 in the desired operating temperature range. This resistance value, e.g. 9–10Ω at 600° C., is known and typically is well defined within a given temperature range. Corresponding current and voltage parameters, e.g., 0.47 A and 4.1 volts, are programmed into the heating circuit controller 50, and the controller 50 is programmed to maintain these values. The actual operating temperature of any individual sensor is held constant within the sensor's operating range.

As an illustrative example, where 1 mil=0.001 inches= 0.0254 mm, a preferred sensor body is 166 mil×124 mil×53 mil (4.22 mm×3.15 mm×1.35 mm) and weighs 144 mg. In the embodiment of the present invention where cover plate heating electrodes 35 are employed, the total electrode overlap area per layer is preferably about 12.7 mm$^2$ and the total area to thickness ratio of the oxygen sensor body 12 is about 199 cm. The exposed edge of each electrode is 50 mil (1.27 mm) wide, and each electrode extends 153 mil (3.89 mm) into the body. The resistive heating electrodes are preferably porous Pt tracks approximately 166 mil (4.22 mm) in length and 22 mil (0.559 mm) in width, whereby a heater current of 223 mA is typical for a control temperature of about 600° C.

Figure 6A:
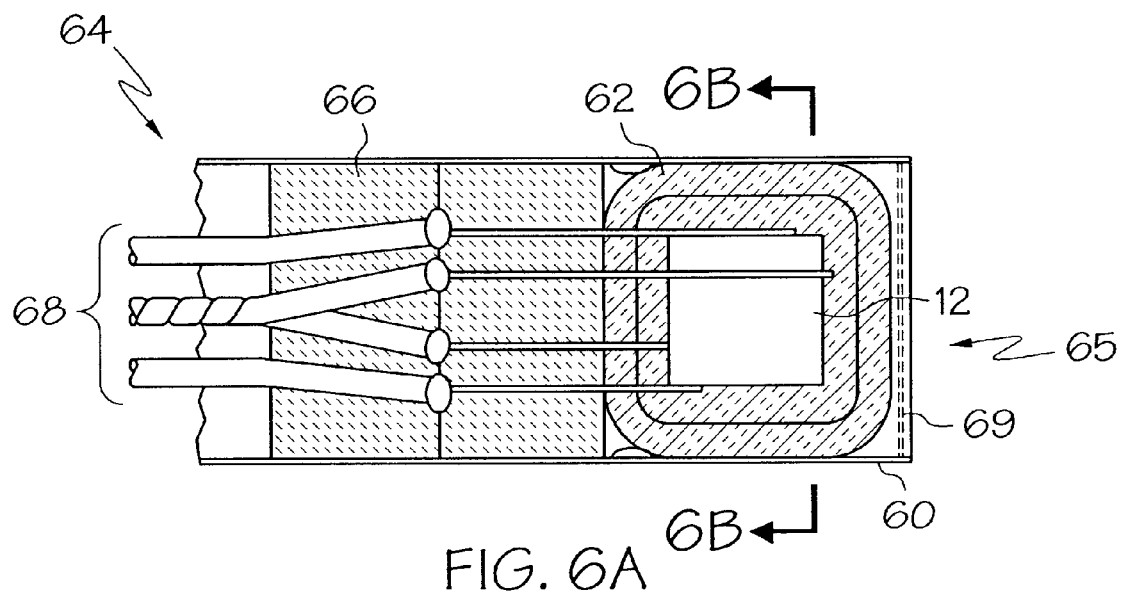
FIGS. 6A and 6B are illustrations of a packaging scheme according to one embodiment of the present invention.
Figure 6B:
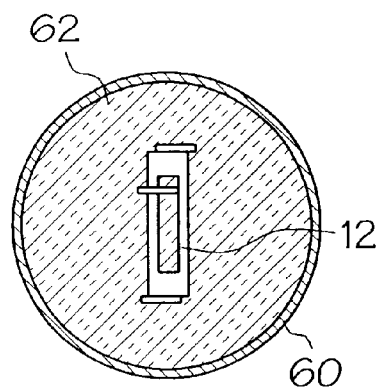

Referring now to FIGS. 6A and 6B, a packaging scheme according to one embodiment of the present invention is illustrated. In the illustrated embodiment, the sensor body 12 is enclosed in a stainless steel tube 60. The thickness of the tube 60 is preferably selected to be machinable for threads for mounting the package into a bulkhead or exhaust flue. The sensor body 12 is stabilized and thermally insulated within the tube 60 by means of suitable gas permeable thermal insulation 62 (e.g., Nextel 312 thermal insulation). A back end 64 of the tube 60 is sealed with a ceramic 66. Electrical connections 68 to the sensor body 12 are potted in the ceramic 66 and routed through the insulation 62. Preferably, the electrical connections comprise 20 gauge copper leads coupled to the four sensor leads. A front end 65 of the tube 60 is provided with a stainless steel screen 69 to permit gas to reach the sensor body 12.

While certain representative embodiments and details have been shown for purposes of illustrating the invention, it will be apparent to those skilled in the art that various changes in the methods and apparatus disclosed herein may be made without departing from the scope of the invention, which is defined in the appended claims. For example, although the sensor 10 of the present invention is well suited for measuring excess oxygen partial pressure because the oxygen-porous terminations 22, 24 present a catalysis area for the combustion of CO and other combustibles, it is noted that the present invention may be arranged for measuring actual oxygen partial pressure rather than excess oxygen partial pressure. Specifically, the cathode electrodes 16$a$, 16$b$ exposed on the first edge 18 of the sensor body 12 are very thin and present a very small catalysis area for the combustion of CO and other combustibles. Accordingly, by omitting the oxygen-porous terminations 22, 24, the sensor 10 of the present invention may be arranged for measuring actual oxygen partial pressure rather than excess oxygen partial pressure.

Further, it is contemplated by the present invention that a pair of sensors could be packaged to yield both actual and excess oxygen measurements simply by providing the oxygen-porous terminations 22, 24 on one sensor body only. Finally, it is noted that an alternate method of measuring actual and excess oxygen using two sensors would be to maintain one sensor below the ignition temperature of CO (600–650° C.) and the second sensor above this temperature, also in a single package.

It is further contemplated that the sensor of the present invention may be arranged for use as a $NO_X$ sensor by utilizing oxygen porous rhodium electrodes in the sensor. Specifically, at elevated temperatures, e.g., above about 600° C., Rh catalyzes the dissociation of $NO_X$ into $N_2$ and $O_2$. Accordingly, dissociated $O_2$ may be measured as an amperometric current and the amperometric current may be related to $NO_X$ content.

What is claimed is:

1. An amperometric oxygen sensor for determining the oxygen partial pressure of a gas, said sensor comprising:
   a multilayer sensor body defined by a plurality of oxygen-porous electrode layers and at least one oxygen ion conductor layer wherein
      said plurality of oxygen-porous electrode layers define an electrode porosity where about 5 to about 30 percent of said electrode layers, by volume, is occupied by pores;
      said plurality of oxygen-porous electrode layers include at least one cathode layer and at least one anode layer, each of said cathode layers defining first and second unexposed major cathode surfaces and each of said anode layers defining first and second unexposed major anode surfaces,
      said oxygen ion conductor layer is interposed between said first major cathode surface and said first major anode surface,
      said cathode layer defines a cathode end portion exposed along a first edge of said sensor body,
      said anode layer defines an anode end portion exposed along a second edge of said sensor body, and
      said multilayer sensor body is configured such that both said first and second edges of said sensor body are adapted to be immersed in said gas,
   a voltage source having a first pole connected to said cathode layer and a second pole connected to said anode layer for generating an oxygen pump potential across said electrode layers, and
   a current meter connected to measure an amperometric current flowing through said at least one ion conductor layer.

2. An amperometric oxygen sensor a claimed in claim 1 wherein about 30 percent of said electrode layers, by volume, is occupied by pores.

3. An amperometric oxygen sensor as claimed in claim 1 wherein:
   an electrically conductive oxygen-porous termination is disposed along said first edge of said sensor body in electrical connection with said cathode end portion;
   an additional electrically conductive oxygen-porous termination is disposed along said second edge of said sensor body in electrical connection with said anode end portion;
   an additional sensor body is disposed in said gas with said sensor body; and
   said additional sensor body includes structure corresponding to the structure of said sensor body with the exception of said electrically conductive oxygen-porous termination and said additional electrically conductive oxygen-porous termination, whereby said amperometric oxygen sensor is operative to yield both actual and excess oxygen measurements of said gas.

4. An amperometric oxygen sensor as claimed in claim 1 wherein:
   an additional sensor body is disposed in said gas with said sensor body; and
   said additional sensor body is configured to be maintained at a temperature different than said sensor body.

5. An amperometric oxygen sensor as claimed in claim 4 wherein:
   said additional sensor body is maintained below an ignition temperature of a combustible gas; and
   said sensor body is configured to be maintained above said ignition temperature.

6. An amperometric oxygen sensor as claimed in claim 5 wherein said combustible gas comprises CO.

7. An amperometric oxygen sensor for determining the oxygen partial pressure of a gas, said sensor comprising:
   a first multilayer sensor body defined by a plurality of oxygen-porous electrode layers and at least one oxygen ion conductor layer wherein
      said plurality of oxygen-porous electrode layers include at least one cathode layer and at least one anode layer, each of said cathode layers defining first and second unexposed major cathode surfaces and each of said anode layers defining first and second unexposed major anode surfaces,
      said oxygen ion conductor layer is interposed between said first major cathode surface and said first major anode surface,
      said cathode layer defines a cathode end portion exposed along a first edge of said sensor body,
      said anode layer defines an anode end portion exposed along a second edge of said sensor body,
      an electrically conductive oxygen-porous termination is disposed along said first edge of said sensor body in electrical connection with said cathode end portion,
      an additional electrically conductive oxygen-porous termination is disposed along said second edge of said sensor body in electrical connection with said anode end portion, and
      said multilayer sensor body is configured such that both said first and second edges of said sensor body are adapted to be immersed in said gas;
   an additional multilayer sensor body disposed in said gas with said sensor body, wherein said additional sensor body includes structure corresponding to the structure of said sensor body with the exception of said electrically conductive oxygen-porous termination and said additional electrically conductive oxygen-porous termination, whereby said amperometric oxygen sensor is operative to yield both actual and excess oxygen measurements of said gas;
   a voltage source having a first pole connected to said cathode layer of said first multilayer sensor body and a second pole connected to said anode layer of said first multilayer sensor body for generating an oxygen pump potential across said electrode layers, and a current meter connected to measure an amperometric current flowing through said at least one ion conductor layer of said first multilayer sensor body.

8. An amperometric oxygen sensor for determining the oxygen partial pressure of a gas, said sensor comprising:

a first multilayer sensor body defined by a plurality of oxygen-porous electrode layers and at least one oxygen ion conductor layer wherein said plurality of oxygen-porous electrode layers include at least one cathode layer and at least one anode layer, each of said cathode layers defining first and second unexposed major cathode surfaces and each of said anode layers defining first and second unexposed major anode surfaces, said oxygen ion conductor layer is interposed between said first major cathode surface and said first major anode surface, said cathode layer defines a cathode end portion exposed along a first edge of said sensor body, said anode layer defines an anode end portion exposed along a second edge of said sensor body, an electrically conductive oxygen-porous termination is disposed along said first edge of said sensor body in electrical connection with said cathode end portion, an additional electrically conductive oxygen-porous termination is disposed along said second edge of said sensor body in electrical connection with said anode end portion, and said multilayer sensor body is configured such that both said first and second edges of said sensor body are adapted to be immersed in said gas;

an additional multilayer sensor body disposed in said gas with said sensor body, wherein said additional sensor body is configured to be maintained at a temperature below an ignition temperature of a combustible gas to provide an actual oxygen measurement of said gas, and said sensor body is configured to be maintained at a temperature above said ignition temperature of said combustible gas to provide an excess oxygen measurement of said gas;

a voltage source having a first pole connected to said cathode layer of said first multilayer sensor body and a second pole connected to said anode layer of said first multilayer sensor body for generating an oxygen pump potential across said electrode layers; and a current meter connected to measure an amperometric current flowing through said at least one ion conductor layer.

9. A method of determining the partial pressure of oxygen in a gas comprising the steps of:

providing an amperometric oxygen sensor comprising a multilayer sensor body defined by a plurality of oxygen-porous electrode layers and at least one oxygen ion conductor layer wherein said plurality of oxygen-porous electrode layers define an electrode porosity where about 5 to about 30 percent of said electrode layers, by volume, is occupied by pores;

said plurality of oxygen-porous electrode layers include at least one cathode layer and at least one anode layer, each of said cathode layers defining first and second unexposed major cathode surfaces and each of said anode layers defining first and second unexposed major anode surfaces, said oxygen ion conductor layer is interposed between said first major cathode surface and said first major anode surface, said cathode layer defines a cathode end portion exposed along a first edge of said sensor body, said anode layer defines an anode end portion exposed along a second edge of said sensor body, said multilayer sensor body is configured such that both said first and second edges of said sensor body are adapted to be immersed in said gas, a voltage source having a first pole connected to said cathode layer and a second pole connected to said anode layer for generating an oxygen pump potential across said electrode layers, and a current meter connected to measure an amperometric current flowing through said at least one ion conductor layer;

immersing said amperometric oxygen sensor in said gas such that both said first and second edges of said sensor body are immersed in said gas;

generating an oxygen pump potential across said electrode layers by connecting a first pole of a voltage source to said at least one cathode layer and a second pole of said voltage source to said at least one anode layer; and measuring an amperometric current flowing through said plurality of oxygen ion conductor layers.

10. A method as claimed in claim 9 further comprising the step of:

disposing an additional sensor body in said gas with said sensor body; and maintaining said additional sensor body at a temperature different than said sensor body.

11. A method as claimed in claim 10 wherein said additional sensor body is maintained below an ignition temperature of a combustible gas and said sensor body is maintained above said ignition temperature of said combustible gas.

12. A method as claimed in claim 11 wherein said combustible gas comprises CO.

* * * * *